US00PP35324P2

(12) United States Plant Patent
Hayano

(10) Patent No.: US PP35,324 P2
(45) Date of Patent: Aug. 22, 2023

(54) MINIATURE ROSE PLANT NAMED 'AYA NO4'

(50) Latin Name: *Rosa hybrida*
Varietal Denomination: AYA NO4

(71) Applicant: The Conard Pyle Company, West Grove, PA (US)

(72) Inventor: Kimiharu Hayano, Honjo (JP)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/095,722

(22) Filed: Jan. 11, 2023

(30) Foreign Application Priority Data

Jan. 19, 2022 (QZ) ..... PBR 2022/0168

(51) Int. Cl.
*A01H 5/02* (2018.01)
*A01H 6/74* (2018.01)

(52) U.S. Cl.
USPC ..... Plt./121
CPC ..... *A01H 6/749* (2018.05)

(58) Field of Classification Search
USPC ..... Plt./121
CPC ..... A01H 6/749; A01H 5/02
See application file for complete search history.

(56) References Cited

U.S. PATENT DOCUMENTS

PP31,646 P3 4/2020 Hayano

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'AYA NO4', is disclosed. The new variety forms attractive, small double pink colored flowers. Attractive semi-glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'AYA NO4'.

CROSS REFERENCE TO RELATED APPLICATIONS

This application claims priority to Plant Breeders' Right Application Number 2022/0168, which was filed at Community Plant Variety Office in the European Union on Jan. 19, 2022, the contents of which are hereby incorporated by reference for all purposes.

STATEMENT REGARDING PRIOR DISCLOSURES BY THE INVENTOR

The first offer for sale of the new variety was Mar. 19, 2021 in Kenya. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was discovered in Spring 2017 in Saitama pref., Japan as a spontaneous mutation of 'AYA NO5' (not patented). The new variety was selected and preserved primarily because of its different pink flower color from the flower color of the 'AYA NO5' parent variety, which is commonly near Red-Purple Group 68B.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms pink colored flowers,
(b) produces small double flowers, and
(c) exhibits a semi-glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'AYA NO5' variety (i.e., parent variety) displays a more compact growth habit compared to the new variety in that the new variety is taller than the 'AYA NO5' variety. Moreover, the new variety can be readily distinguished from other similar non-parental varieties. For example, the 'HOHOEMI ROUGE' variety (U.S. Plant Pat. No. 31,646) has darker pink colored flowers and longer stems compared to the new variety.

The new variety has been named 'AYA NO4'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during June while budded by cuttings and growing in greenhouses at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—obverse.

Element 8—illustrates a specimen of a fully open flower—plan view—reverse.

Element 9—illustrates a specimen of a fully open flower—plan view—obverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 5 leaflets—plan view—upper surface.

Element 15—illustrates a specimen of a leaf with 7 leaflets—plan view—upper surface.

Element 16—illustrates flowers and buds in cluster.

Element 17—illustrates a specimen of a leaf with 3 leaflets—plan view—under surface.

Element 18—illustrates a specimen of a leaf with 5 leaflets—plan view—under surface.

Element 19—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of one-year-old specimens of the new variety during June while budded by cuttings and growing in greenhouses at Le Cannet des Maures, Var, France.

Botanical classification: *Rosa hybrida* cultivar 'AYA NO4'.

Commercial classification: Miniature Rose Plant.

Plant:

*Habit*.—Bushy.

*Height*.—Approximately 70 cm on average.

*Width*.—Approximately 70 cm on average.

Branches:

*Color*.—Young stems: commonly near Yellow-Green Group 144A. — adult wood: commonly near Yellow-Green Group 146A.

*Length*.—From the crown to the flower is typically between 45 cm to 55 cm.

*Diameter*.—Typically between 0.4 to 0.6 cm on average.

*Young shoots*.—Anthocyanin coloration: slight, commonly near Greyed-Red Group 178A.

*Thorns*.—Configuration on adult stems: concave and elongated on the upper surface and very concave on the under surface. — long prickles — quantity: approximately 7 thorns on average per 10 cm long young stem and approximately 8 thorns on average per 10 cm long adult stem. — long prickles — length: typically between 0.3 cm to 0.5 cm on young stems and typically between 0.4 cm to 0.6 cm on adult stems. — long prickles — width: approximately 0.1 cm on average on young stems and approximately 0.1 cm on average on adult stems. — long prickles — base: shape is very narrow and elliptic on young stems; shape is narrow and obovate on adult stems. — long prickles — color on young stems: commonly near Yellow-Green Group 1526 at the tip and near Greyed-Orange Group 166D at the base. — long prickles — color on adult stems: commonly near Greyed-Orange Group 165B at the tip and near Greyed-Orange Group 165A at the base. — small prickles — quantity: absent.

*Internode*.—Numbers on the entire branch: approximately 7 on average. — length: typically between 2.8 cm and 4.3 cm.

Foliage:

*General appearance*.—Rather dense with a semi-glossy aspect.

*Number of leaflets*.—3, 5, 7; most often 7.

7 *leaflets leaf*.—Length: typically between 7.2 cm to 11.1 cm. — width: typically between 4.1 cm to 7.5 cm.

*Terminal leaflet*.—Length: typically between 3.3 cm to 4.9 cm. — width: typically between 1.5 cm to 2.7 cm.

*New foliage*.—Upper surface color: commonly near Yellow-Green Group 146A. — under surface color: commonly near Yellow-Green Group 146A slightly suffused with anthocyanin coloration near Greyed-Purple Group 183A.

*Adult foliage*.—Upper surface color: commonly near Green Group 137A. — under surface color: commonly near Green Group 137C. — anthocyanin coloration: absent.

Leaflets:

*Shape*.—Tip: cuneiform. — base: pointed.

*Glossiness of upper surface*.—Medium.

*Texture*.—Upper and under surfaces are thick.

*General appearance*.—Oval.

*Serration*.—Small and single.

*Undulation on the margin*.—Very weak.

*Venation*.—Color is commonly near Green Group 137A and pattern is imparipinnate.

*Petiole rachis*.—Color of upper surface: commonly near Green Group 137A. — color of under surface: commonly near Yellow-Green Group 144A. — texture: upper surface is no glandular, under surface is smooth with very few prickles. — rachis of terminal leaflet: length is typically between 2.0 cm to 4.0 cm on average and diameter is approximately 0.1 cm on average.

*Petioles*.—Upper surface: no glandular. — under surface: no prickles. — color of upper surface: commonly near Green Group 137A. — color of under surface: commonly near Yellow-Green Group 144A. — length: typically between 0.8 cm to 1.8 cm. — diameter typically between 0.1 cm to 0.2 cm.

*Stipules*.—Length: approximately 0.5 cm on average. — width: approximately 0.2 cm on average. — general appearance: narrow. — texture: smooth. — color of upper surface: commonly near Yellow-Green Group 146C suffused with near Yellow-Green Group 146B. — color of under surface: commonly near Yellow-Green Group 146B suffused with near Yellow-Green Group 147A.

Inflorescence:

*Number of flowers per stem*.—Typically between 5 to 30 flowers per stem.

*Lastingness of the bloom*.—On the plant: approximately 3 weeks. — in vase: 15 days on average.

*Bud*.—Shape: ovoid. — size: small. — length: approximately 0.8 cm on average. — width: approximately 0.7 cm on average. — color as calyx breaks: upper surface: commonly near Red Group 49D, basal spot is very little and commonly near Greyed-Green Group 195D. under surface: commonly near Red Group 50D suffused with near Red Group 55C, basal spot is very little and commonly near Greyed-Green Group 195D.

*Sepals*.—Number commonly 5. — length: approximately 1.0 cm on average. — width: approximately 0.3 cm on average (on median part). — shape: at the top: elongated and narrow. at the base: upright. — extensions: typically 3 sepals with weak extensions and 2 sepals without extensions. — upper surface: texture: slightly tomentous. color commonly near Yellow-Green Group 146C at the base and near Yellow-Green Group 147C at the top. — under surface: texture: glandular. color commonly near Yellow-Green Group 146B at the base and near Yellow-Green Group 146A at the top.

*Receptacle*.—Color: commonly near Yellow-Green Group 144A. — length: approximately 0.5 cm on average. — width: approximately 0.25 cm on average. — surface: smooth. — shape: pear shaped.

*Peduncle*.—Length: approximately 3.0 cm on average. — width: approximately 0.1 cm on average. — surface: glandular. — color: commonly near Yellow-Green Group 144A.

*Flower*.—Diameter when open: approximately 2.5 cm on average. — depth of the flower typically between 1.0 cm to 1.5 cm. — shape: cup shaped. — shape when viewed from above: irregular rounded. — shape of the upper part of the flower profile: flat. — shape of the lower part of the flower profile: flat. — type: double. — number of petals under normal conditions: typically between 20 to 30 petals. — petals: shape: cordiform (acute at the base and indented at the top). texture: thick. length: typically between 0.8 cm to 1.1 cm. width: typically between 0.6 cm to 1.0 cm. — undulation of the petal: very weak. — reflexing of the petal: strong toward the inside for the most internal petals. — petal incision: very weak. — petal arrangement: imbricated without petaloids. — petal drop: petals drop off cleanly before drying. — fragrance: none. — discoloration of the flower: none. — color when opening: basal spot on the upper surface: commonly near Greyed-Green Group 196D. upper surface: commonly a color between Red Group 55C and Red Group 55B, flecked with near Red Group 55A. basal spot on the under surface: commonly near Greyed-Green Group 196D. under surface: commonly a color between near Red Group 55B and near Red Group 55D, slightly suffused with near Red Group 54D. — color of the open flower: basal spot on the upper surface: commonly near Greyed-Green Group 196D. upper surface of the flower: commonly a color between Red Group 55D and Red Group 54D, flecked with near Red Group 55A. basal spot on the under surface: commonly near Greyed-Green Group 196D. under surface of the flower: commonly a color between near Red Group 55B and near Red Group 55D, slightly suffused with near Red Group 51D. — anthers: number is typically between 25 to 40, length is approximately 0.15 cm on average, width is approximately 0.1 cm on average, coloration is commonly near Yellow-Orange Group 22A, and arrangement is regular around styles. — filaments: length is approximately 0.4 cm on average and coloration is commonly near Yellow Group 3C. — styles: length is typically between 0.3 cm to 0.4 cm, coloration is commonly near Yellow-Green Group 154C, and number is typically between 5 to 10. — stigmas: length is approximately 0.1 cm on average and coloration is commonly near Yellow-Green Group 154D. — pollen: color is commonly near Greyed-Orange Group 163B and quantity is medium. — hips: not observed.

Development:

*Vegetation*.—Strong.

*Blooming*.—Medium in the season, abundant and recurrent, typically from May to first frost in France.

*USDA hardiness zone*.—Zone 5 to 10.

*Tolerance to disease*.—Good, and particularly against rust (*Phragmidium mucronatum*).

The new 'AYA NO4' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'AYA NO4' characterized by the following combination of characteristics:

(a) forms pink colored flowers, (b) produces small double flowers, and (c) exhibits a semi-glossy foliage;

substantially as herein shown and described.

* * * * *

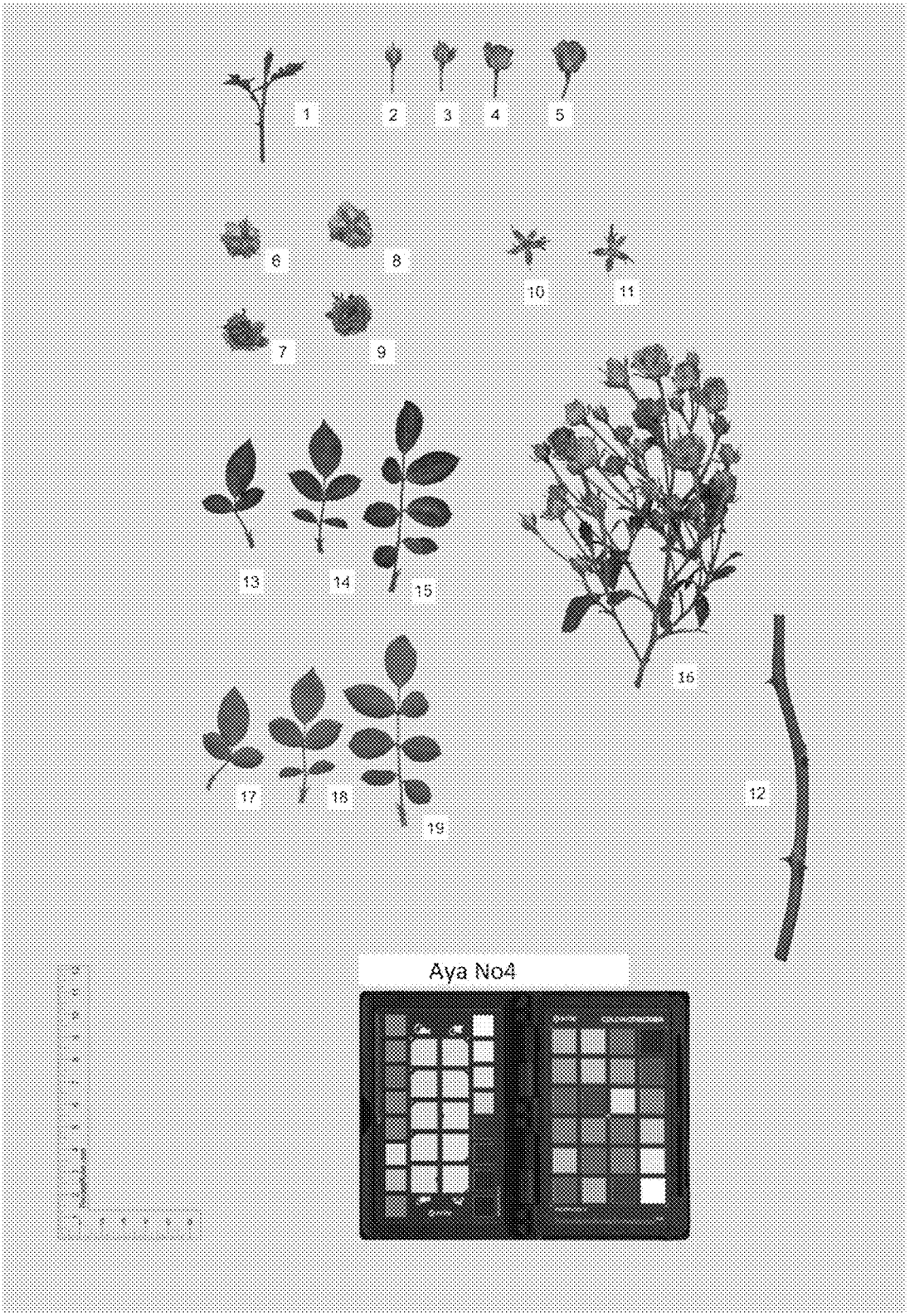
1
2
3
4
5
6
8
10
11
7
9
13
14
15
16
17
18
19
12
Aya No4